United States Patent
De Haan (10) Patent No.: US 10,478,078 B2
(45) Date of Patent: Nov. 19, 2019

(54) DEVICE AND METHOD FOR DETERMINING VITAL SIGNS OF A SUBJECT

(71) Applicant: KONINKLIJKE PHILIPS N.V., Eindhoven (NL)

(72) Inventor: Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 268 days.

(21) Appl. No.: 15/102,649

(22) PCT Filed: Nov. 28, 2014

(86) PCT No.: PCT/EP2014/075879
§ 371 (c)(1),
(2) Date: Jun. 8, 2016

(87) PCT Pub. No.: WO2015/086338
PCT Pub. Date: Jun. 18, 2015

(65) Prior Publication Data
US 2016/0302679 A1    Oct. 20, 2016

(30) Foreign Application Priority Data
Dec. 12, 2013 (EP) .................................. 13196831

(51) Int. Cl.
*A61B 5/024* (2006.01)
*A61B 5/00* (2006.01)
*A61B 5/1455* (2006.01)

(52) U.S. Cl.
CPC ........ *A61B 5/02416* (2013.01); *A61B 5/0077* (2013.01); *A61B 5/1455* (2013.01); *A61B 5/7203* (2013.01); *A61B 5/725* (2013.01)

(58) Field of Classification Search
CPC ..... A61B 5/72–5/7296; A61B 5/02416; A61B 5/7203; A61B 5/7207
See application file for complete search history.

(56) References Cited

U.S. PATENT DOCUMENTS 7,209,774 B2 *  4/2007  Baker, Jr. ........... A61B 5/14551
                                                      600/323
2005/0010116 A1   1/2005  Korhonen et al.
(Continued)

FOREIGN PATENT DOCUMENTS

RU    2008108991 A    9/2009
WO    2007017777 A2   2/2007
(Continued)

OTHER PUBLICATIONS

Huang et al: "Hilbert-Huang Transform"; Scholarpedia, 8 Page Article, 2008, 3(7):2544.
(Continued)

*Primary Examiner* — Michael W Kahelin (57) ABSTRACT

The present invention relates to a Device for determining vital signs of a subject comprising an interface (22) for receiving a periodic photoplethysmographic, PPG, signal obtained from a subject (14) by a PPG measurement, a signal partitioning unit (24) for partitioning the PPG signal in time into a plurality of PPG sub-signals covering a half period or an integer multiple of a half period, a normalizing unit (26) for normalizing the PPG signal in advance of the partitioning and/or the PPG sub-signals in time and/or amplitude, a signal combination unit (28) for combining a number of normalized PPG sub-signals to obtain a combined PPG sub-signal, and a vital sign processor (30) for deriving a desired vital sign from the PPG signal, one or more combined PPG sub-signals or an enhanced PPG signal obtained by consecutively arranging a number of combined PPG sub-signals.

15 Claims, 7 Drawing Sheets

(56) References Cited

U.S. PATENT DOCUMENTS

| | | |
|---|---|---|
| 2005/0197579 A1 | 9/2005 | Baker, Jr. |
| 2006/0217615 A1 | 9/2006 | Huiku et al. |
| 2008/0027341 A1 | 1/2008 | Sackner et al. |
| 2009/0043179 A1 | 2/2009 | Melker et al. |
| 2009/0326388 A1 | 12/2009 | Watson et al. |
| 2013/0158417 A1 | 6/2013 | Borger |

FOREIGN PATENT DOCUMENTS

| | | |
|---|---|---|
| WO | 2009147597 A1 | 12/2009 |
| WO | 2011077294 A1 | 6/2011 |
| WO | 2013027027 A2 | 2/2013 |

OTHER PUBLICATIONS

Hlimonenko et al: "Waveform Analysis of Peripheral Pulse Wave Detected in the Fingertip With Photoplethysmograph"; Measurement Science Review, vol. 3, Section 2, 2003, pp. 49-52.

Verkruysse et al: "Remote Plethysmographic Imaging Using Ambient Light"; OPT Express, 2008, vol. 16(26) pp. 1-16.

Wieringa et al: "Contactless Multiple Wavelength Photoplethysmographic Imaging: A First Step Toward "SpO2 Camera" Technology"; Annals of Biomedical Engineering, vol. 33, No. 8, Aug. 2005, pp. 1034-1041.

Parker: "3. Ensemble Averaging"; Dec. 2012, XP055118347, Retrieved From The Internet at http://www.bg.ic.ac.uk/research/k.parker/guide_to_wia/03_ensemble_average.html on May 15, 2014, 11 Page Document.

* cited by examiner

DEVICE AND METHOD FOR DETERMINING VITAL SIGNS OF A SUBJECT

CROSS-REFERENCE TO PRIOR APPLICATIONS

This application is the U.S. National Phase application under 35 U.S.C. § 371 of International Application No. PCT/EP2014/075879, filed on Nov. 28, 2014, which claims the benefit of European Patent Application No. 13196831.5, filed on Dec. 12, 2013. These applications are hereby incorporated by reference herein.

FIELD OF THE INVENTION

The present invention relates to a device and a method for determining vital signs of a subject, such as a person or animal.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue colour channels.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Using PPG technology, vital signs can be measured, which are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations, with severe motion, challenging environmental illumination conditions, or high required accuracy of the application, where an improved robustness and accuracy of the vital sign measurement devices and methods is required, particularly for the more critical healthcare applications.

US 2005/197579A1 discloses a method and device for detecting the presence of mixed venous and arterial blood pulsation in tissue, including receiving first and second electromagnetic radiation signals from a blood perfused tissue portion corresponding to infrared and red wavelengths of light, obtaining a measure of a phase difference between the first and second electromagnetic radiation signals, comparing the measure with a threshold value to form a comparison, and detecting the presence or absence of venous pulsation using the comparison.

US 2006/217615 A1 discloses the determination of the clinical stress of a subject. In order to bring about an uncomplicated and cost-effective method for monitoring the stress status of a subject, plethysmographic signal data is acquired from the subject and a first measurement signal is derived, which is indicative of a predetermined feature of the respiration modulation appearing in the said signal data. An index signal is then formed based on the first measurement signal and the index signal is employed as an index indicative of the clinical stress of the subject.

WO 2013/027027 A2 discloses a method of remote monitoring of vital signs by detecting the PPG signal in an image of a subject taken by a video camera such as a webcam. The PPG signal is identified by auto-regressive analysis of ambient light reflected from a region of interest on the subject's skin. Frequency components of the ambient light and aliasing artefacts resulting from the frame rate of the video camera are cancelled by auto-regressive analysis of ambient light reflected from a region of interest not on the subject's skin, e.g. in the background. This reveals the spectral content of the ambient light allowing identification of the subject's PPG signal. Heart rate, oxygen saturation and breathing rate are obtained from the PPG signal. The values can be combined into a wellness index based on a statistical analysis of the values.

SUMMARY OF THE INVENTION

It an object of the present invention to provide an improved device and method for determining vital signs of a subject having an increased signal-to-noise ratio and efficiency in reduction of artefacts caused by distortions, in particular by motion of the subject.

In a first aspect of the present invention a device for determining vital signs of a subject is presented, the device comprising:
- an interface for receiving a periodic photoplethysmographic, PPG, signal obtained from a subject by a PPG measurement,
- a signal partitioning unit for partitioning the PPG signal in time into a plurality of PPG sub-signals covering a half period or an integer multiple of a half period,
- a normalizing unit for normalizing the PPG signal in advance of the partitioning and/or the PPG sub-signals in time and/or amplitude,
- a signal combination unit for combining a number of normalized PPG sub-signals to obtain a combined PPG sub-signal, and
- a vital sign processor for deriving a desired vital sign from the PPG signal, one or more combined PPG sub-signals or an enhanced PPG signal obtained by consecutively arranging a number of combined PPG sub-signals.

In a further aspect of the present invention a corresponding method is presented.

In yet further aspects of the present invention, there are provided a computer program which comprises program code means for causing a computer to perform the steps of the method when said computer program is carried out on a computer as well as a non-transitory computer-readable recording medium that stores therein a computer program product, which, when executed by a computer processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

The present invention is based on the idea to improve the signal through enhancing the waveform (i.e. the PPG signals) obtained from either a contact PPG or a camera rPPG device. A possibly adaptive, recent history of beat-to-beat waveforms is normalized in time and/or amplitude and combined to create an enhanced (or synthesized) waveform with more relevant physiological meaning. This enhanced waveform is used to, at least partially, replace or supplement the actual beat-to-beat waveform to produce a real-time enhanced pulse signal (i.e. an enhanced PPG signal). One or more vital signs may then be obtained with higher accuracy and robustness from the original PPG signal, one or more combined PPG sub-signals or an enhanced PPG signal obtained by consecutively arranging a number of combined PPG sub-signals.

For instance, in an embodiment it is proposed to compute a combined PPG sub-signal and display a (optionally normalized (in time and amplitude)) PPG sub-signal in addition to the raw (original) PPG signal. In this case the shape information could be observed from the (single period, stationary on the display) combined PPG sub-signal, while the regularity could be observed from the (possibly not-enhanced and moving over the display) original PPG signal.

In another embodiment a number of combined PPG sub-signals are consecutively arranged to obtain an enhanced PPG signal, from which the one or more vital signs are then obtained.

Thus, by using and/or combining normalized PPG sub-signals for deriving vital signs the negative effects of distortions and motion are efficiently reduced.

The resulting enhanced PPG signal reproduces, when measured repeatedly from identical skin segments, while preferably show differences when measured from different locations, or from persons with known pathologies. This enables new applications for the remote PPG technology, which are currently only demonstrated with contact PPG sensors. The same technology could further be applied to bring the quality of the signals obtained from contact sensors to the next level.

The interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (i.e. a living being) and derivative parameters. In particular, the term "vital sign" comprises blood volume pulse-signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), body temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or maybe even about the temperature, etc.).

The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

In an embodiment said signal combination unit is configured to consecutively arrange a combined PPG sub-signals according to the chronological order of the normalized PPG sub-signals, from which they have been obtained. Preferably, said signal combination unit is configured to combine a predetermined number of consecutive normalized PPG sub-signals arranged within a time window to obtain a combined PPG sub-signal, wherein the time window is shifted in time for each combined PPG sub-signal. Thus, a kind of sliding time window, which is slid in time, is used for selecting the normalized PPG sub-signals which are combined into a combined PPG sub-signal. In this way, the original time sequence of the PPG signal can be reconstructed.

In another embodiment said signal partitioning unit is configured to detect zero-crossings and/or extrema (peaks and/or valleys) of the PPG signal and to use the detected zero-crossings and/or extrema for partitioning the PPG signal. For instance, a PPG-sub-signals obtained by this partitioning can span half a period (e.g. from one zero-crossing to the next zero-crossing or from a peak to the subsequent valley) or a complete period (e.g. from one peak to the next peak, from one valley to the next valley, or from a zero-crossing to the next but one zero-crossing). A subsequent normalization in time then ensures that the time length of the PPG sub-signals is equal.

Preferably, the normalizing unit is configured to normalize the PPG signal in advance of the partitioning by detecting extrema of the PPG signal, fitting a first curve through detected peaks and a second curve through detected valleys, subtracting the momentary average value of the first and second curves from the momentary signal value of the PPG signal and dividing the momentary resulting value by the momentary difference value of the first and second curves to obtain a normalized signal value of the PPG signal. This provides for another improvement of the accuracy and robustness of the obtained vital signs.

Advantageously the normalizing unit is configured to repeat the normalization until a stop condition is met or normalized signal value obtained from the normalizations converge, by which the SNR of the enhanced PPG signal can potentially be further improved.

For the combination of the normalized PPG sub-signals various options exist. In an embodiment the signal combination unit is configured to generate an average, a weighted average or a trimmed mean of two or more normalized PPG sub-signals, in particular of all (up to the current time-interval, but limited to a "reasonable" history (e.g. up to a few minutes, but likely much longer histories have decreasing value)) normalized PPG sub-signals. It has been shown that these embodiments provide good results.

In another embodiment the signal combination unit is configured to generate a weighted average or a trimmed mean of two or more normalized PPG sub-signals, in particular of all normalized PPG sub-signals, wherein the weight for weighting normalized PPG sub-signals decreases with the time-distance to the current time interval. Thus, the influence of a recent PPG sub-signal is higher compared to earlier PPG sub-signals in the generation of the combined PPG sub-signal.

Preferably, the device further comprises a filter for low-pass or band-pass filtering the received PPG signal, wherein the filtered PPG signal is used for subsequent processing. This ensures that frequency components in the PPG signal which are out of the typical range of frequency of the desired vital sign are deleted from the PPG signal in advance.

In another embodiment the combination unit is configured to scale the period of the combined PPG sub-signals in time to match the period of the current time interval and to consecutively arrange a number of the scaled combined PPG sub-signals to obtain the enhanced PPG signal. Thus, the combined PPG sub-signals are re-scaled in time to the original period as provided in the original PPG signal before the generation of the enhanced PPG signal. In this way, the enhanced PPG signal can e.g. be displayed simultaneously to or instead of the original PPG signal, e.g. as an overlay, to visualize the improvement, or to only show the enhanced signal to prevent confusion. This makes it possible to show the noise-reduced (or enhanced) PPG signal instead of the current PPG signal. The currently shown PPG signal is also not necessarily the raw signal, but various filtering/processing operations may have been applied to improve the signal. Thus, the present embodiment thus provides a further improvement to the pulse signal which cannot be achieved with current processing/filtering.

In still another embodiment the device further comprises a boosting filter for boosting of high-frequency harmonics in the PPG sub-signals and/or the enhanced PPG signal. This allows for easier visual discrimination of different waveforms.

In still another embodiment the device further has access to a number of PPG signals obtained from different wavelengths, or color-channels (e.g. red, infrared, red, green, blue), wherein an enhanced PPG signal (that may be derived from one or more color channels and successively enhanced as described above is used for subsequent processing to calculate a vital sign. For certain vital signs certain color ranges within a PPG signal have shown best results, e.g. the relative amplitude ratio of the wavelength interval around 650 nm (red) and 840 nm (infrared) has been shown to give clear information about the oxygenation level of the blood (SpO2). Hence, if such a certain vital sign shall be calculated it may profit from the availability of a clean (enhanced) PPG signal. The noise in the ratio of relative amplitudes can be reduced by computing the ratio of the correlations of red and infrared PPG-signals with the enhanced PPG-signal. Alternatively, it is possible to convolve the red and infrared PPG-signals with a matched filter derived from the enhanced PPG-signal.

In a preferred embodiment the proposed device further comprises an imaging unit, in particular a camera such as a video camera, for acquiring image frames of a subject, and a PPG signal generator for deriving a PPG signal from a skin portion of the subject shown in the image frames and for providing the PPG signals to the interface. The imaging unit can comprise one or more imaging elements. For instance, the imaging unit can comprise an array of photodiodes or charge-coupled devices.

In an alternative embodiment the proposed device further comprises a PPG sensor for acquiring PPG signals from a PPG measurement at a skin portion of the subject and for providing the PPG signals to the interface.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
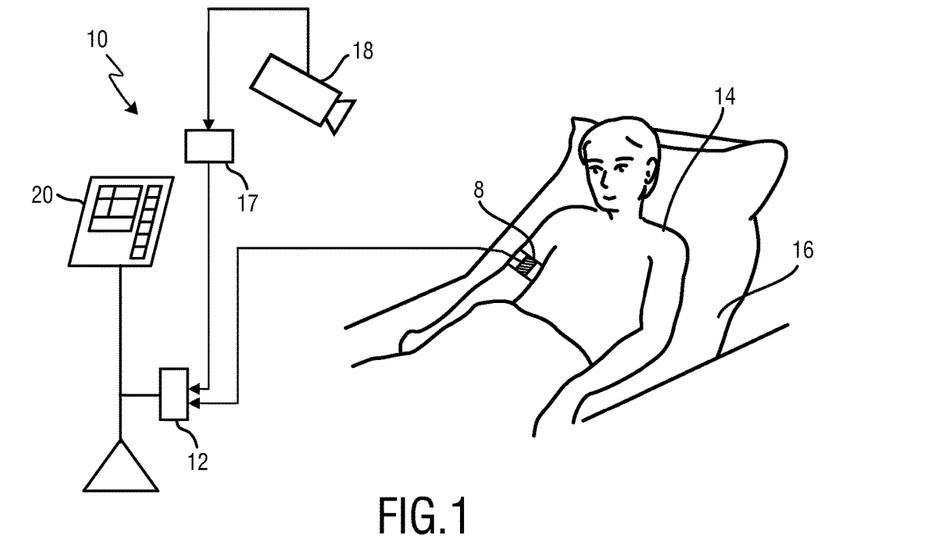
FIG. 1 shows a schematic diagram of a monitoring system including a first embodiment of a device according to the present invention.

FIG. 1 shows a schematic diagram of a monitoring system 10 including a device 12 for obtaining vital signs of a subject 14 according to the present invention. The subject 14, in this example a patient, lies in a bed 16, e.g. in a hospital or other healthcare facility, but may also be a neonate or premature infant, e.g. lying in an incubator, or person at home or in a different environment. Image frames of the subject 14 are captured by means of a camera 18 (also referred to as camera-based, or remote PPG sensor, or imaging unit) including a suitable photosensor. The camera 18 forwards the recorded image frames to the device 12. The device 12 is further connected to an interface 20 for displaying the determined information and/or for providing medical personnel with an interface to change settings of the device 12, the camera 18 or the monitoring system 10. Such an interface 20 may comprise different displays, buttons, touch-screens, keyboards or other human machine interface means. Alternatively or in addition to the camera, a PPG sensor 8 (also referred to as contact PPG sensor), e.g. in form of a finger-clip for measuring the blood oxygen saturation, a heart rate sensor and/or an accelerator for measuring the breathing rate, just to name a few of all the possible embodiments.

The image frames captured by the camera 18 may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera 18 may provide an analog or digital signal. The image frames from the camera 18 include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of photosensitive elements. A PPG signal generator 17 is provided in this embodiment for deriving a PPG signal from a skin portion of the subject shown in the image frames.

A monitoring system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, or the like. The uni- or bidirectional communication between the device 12, the camera 18 and the interface 20 may work via a wireless or wired communication interface. Other embodiments of the present invention may include a device 12, which is not provided stand-alone, but integrated into the camera 18 or the interface 20.

Figure 2:
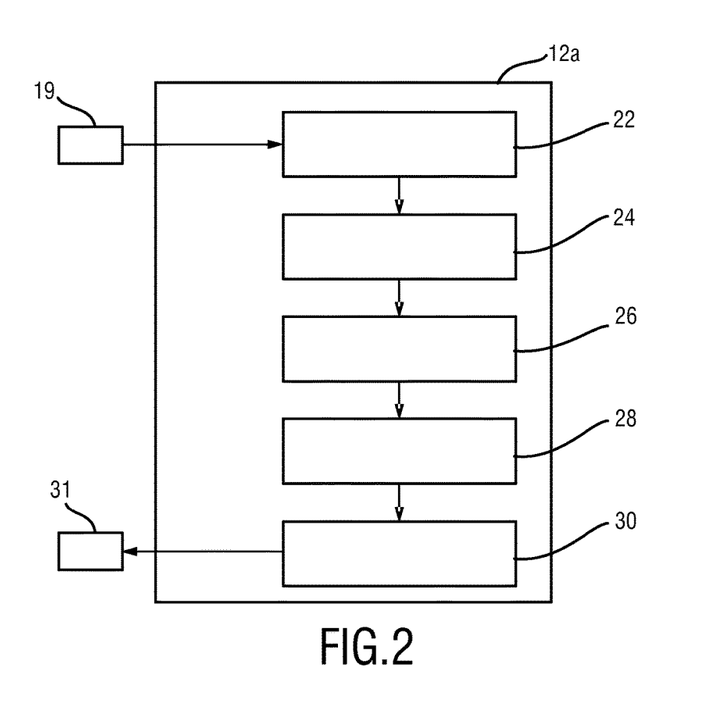
FIG. 2 shows a schematic diagram of a first embodiment of a device according to the present invention.

FIG. 2 shows a more detailed schematic illustration of a first embodiment 12a of the device 12 according to the present invention. The device 12a comprises an interface 22 for receiving a periodic photoplethysmographic (PPG) signal 19 obtained from the subject 14 by a PPG measurement. Said PPG signal 19 can be derived from a set of image frames obtained by the camera 18 or from a sensor 8. The interface 22 may correspond to a wired or wireless network connection, any kind of serial connection or another standard or non-standard communication interface.

Figure 3A:
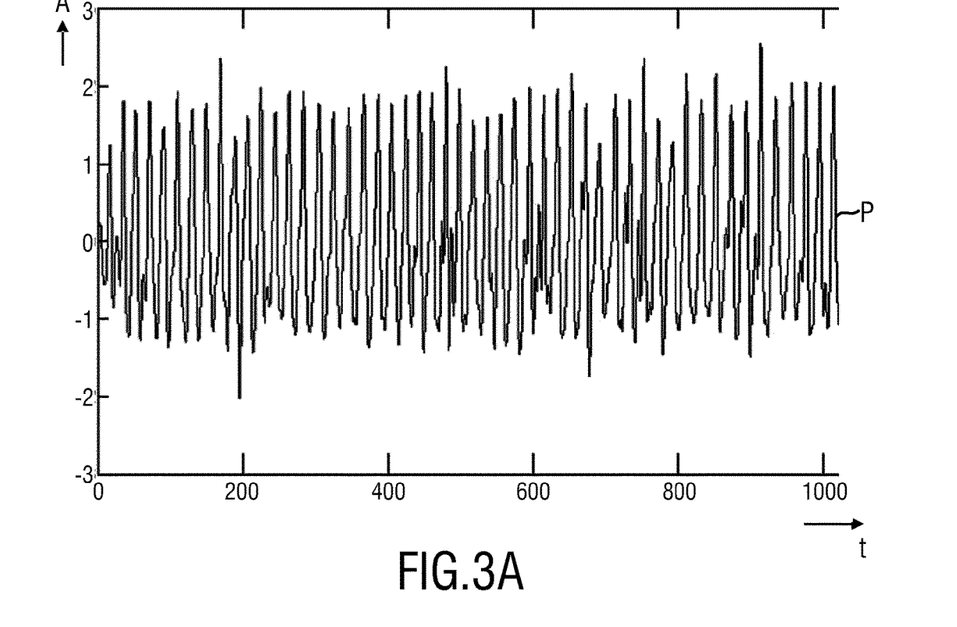
FIG. 3 shows a diagram of a typical PPG signal and an enlarged portion of a PPG signal for illustration of partitioning of the PPG signal into PPG sub-signals.
Figure 3B:
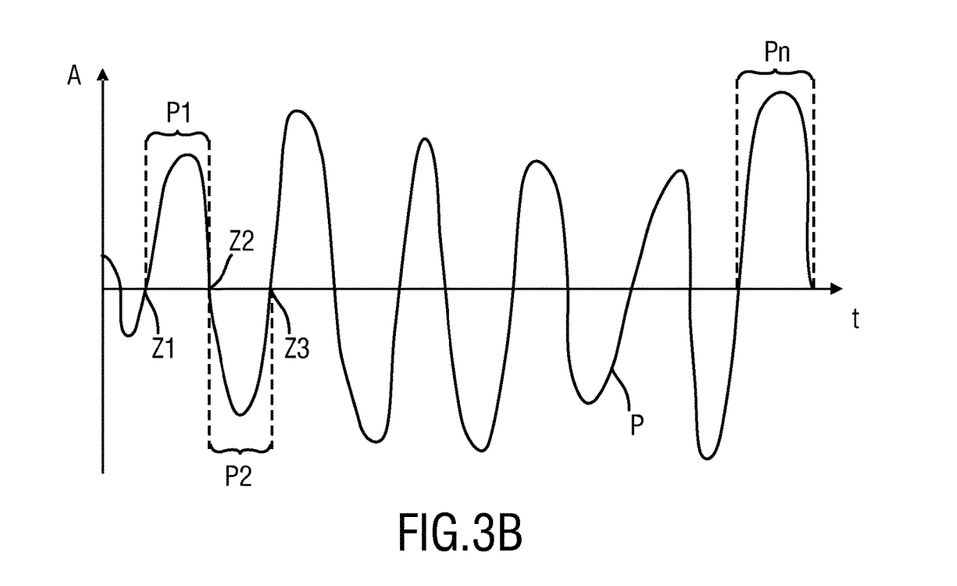

The device 12a further comprises a signal partitioning unit 24 for partitioning the PPG signal in time into a plurality of PPG sub-signals covering a half period or an integer multiple of a half period. This is schematically illustrated in FIG. 3B showing an enlarged view (stretched in time) of a PPG signal P (with its amplitude A versus time t) shown in FIG. 3A. FIG. 3A shows the typical waveform of a PPG signal P obtained from a semi-stationary subject using remote PPG technology. Although the pulse signal is obtained with a rather high SNR, the waveform shows a relatively high variability due to motions and other non-physiological distortions. FIG. 3B shows the partitioning of the PPG signal into PPG sub-signals P1, P2, . . . , Pm. In this embodiment a PPG sub-signal spans over a complete period of the PPG signal P from one zero-crossing to the next but one zero-crossing, e.g. the first PPG-sub-signal P1 spans from the first zero-crossing Z1 to the third zero-crossing Z3, the second PPG-sub-signal P2 spans from the third zero-crossing Z3 to the fifth zero-crossing Z5, etc. In practice it is best to determine the zero-crossing on the steepest edge of the PPG signal as this suffers least from noise. In other embodiments the PPG sub-signals span over one half period or over three or more half periods. Still further, instead of using zero-crossings as start and end points of a PPG sub-signal, other characteristic (easily detectable) points of the PPG signal may be used, such as the peaks or valleys.

The device 12a further comprises a normalizing unit 26 for normalizing the PPG signal in advance of the partitioning by the signal partitioning unit 24 and/or the PPG sub-signals obtained from the signal partitioning unit 24 in time and/or amplitude, preferably both in time and amplitude. In both cases, as a result the (normalized) PPG sub-signals have substantially the same time duration and/or amplitude.

Figure 4:
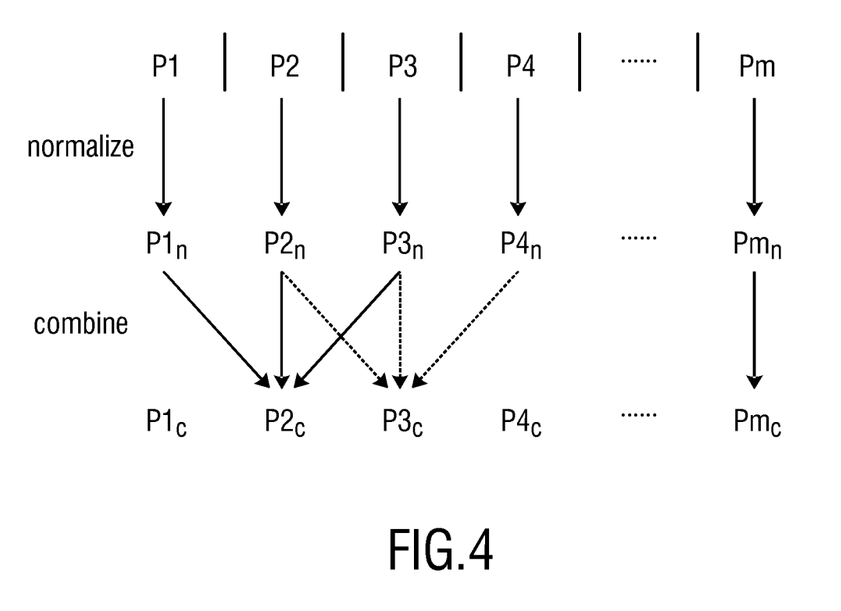
FIG. 4 shows a diagram schematically illustration the combination of PPG sub-signals.

The device 12a further comprises a signal combination unit 28 for combining a number of normalized PPG sub-signals to obtain a combined PPG sub-signal and, optionally, for consecutively arranging a number of combined PPG sub-signals to obtain an enhanced PPG signal. This is schematically illustrated in FIG. 4 showing an embodiment of such a combination. In this embodiment normalized PPG sub-signals $P1_n$, $P2_n$, . . . , $Pm_n$, which may be normalized version of the PPG sub-signals P1, P2, . . . , Pn shown in FIG. 3B, are combined into combined PPG sub-signals $P1_c$, $P2_c$, . . . , $Pm_c$. For instance, the normalized PPG sub-signals $P1_n$, $P2_n$, $P3_n$ are combined to obtain the combined PPG sub-signal $P2_c$, the normalized PPG sub-signals $P2_n$, $P3_n$, $P4_n$ are combined to obtain the combined PPG sub-signal $P3_c$, etc. If a PPG sub-signal spans only a half period, only each second PPG sub-signal may be used for a combination into a combined PPG sub-signal.

Thus, the combination is preferably done such that a predetermined number of consecutive normalized PPG sub-signals arranged within a time window are combined to obtain a combined PPG sub-signal, wherein the time window is shifted in time for each combined PPG sub-signal, which time window spans over three periods in the example depicted in FIG. 4.

Figure 5A:
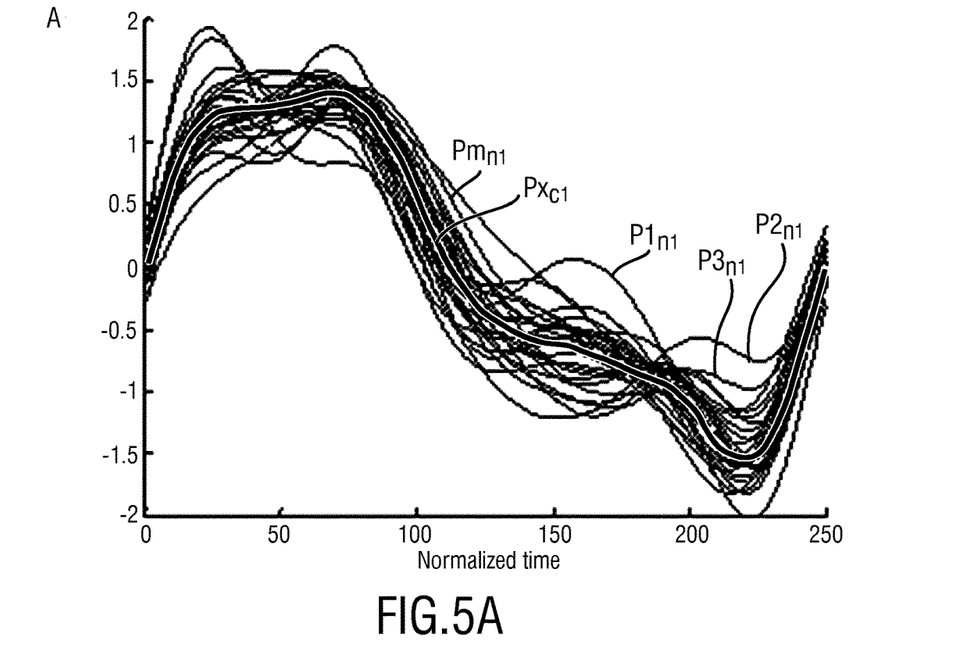
FIG. 5 shows two examples of obtained combined PPG sub-signals.
Figure 5B:
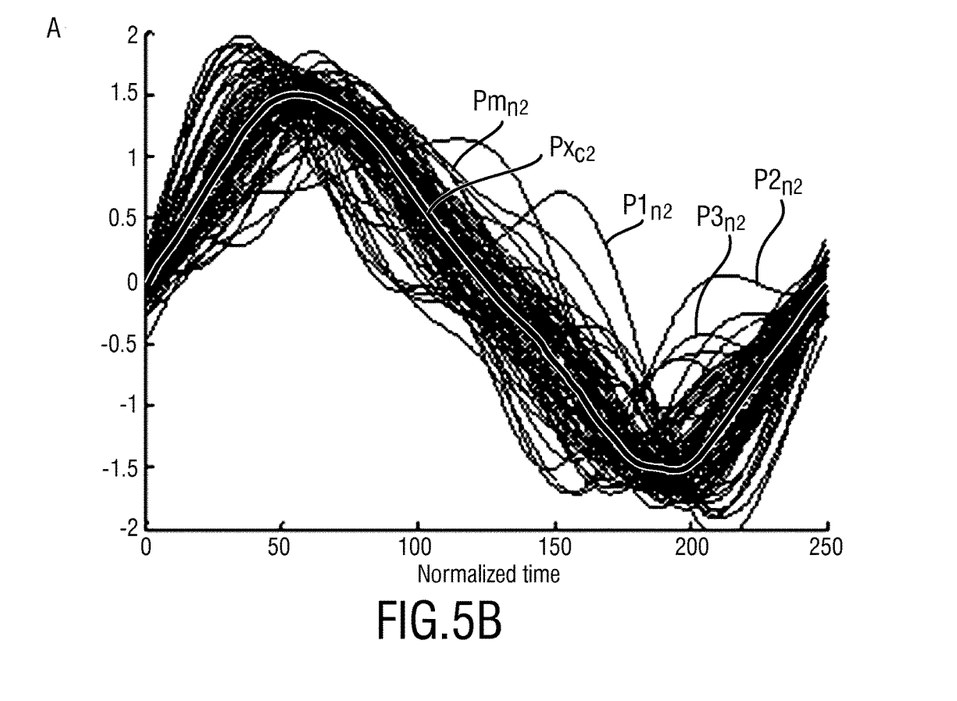

The result of such a combination is shown in FIGS. 5A, 5B, each showing a number of normalized PPG sub-signals $P1_{n1}, P2_{n1}, \ldots, Pm_{n1}$ (for FIG. 5A) and $P1_{n2}, P2_{n2}, \ldots, Pm_{n2}$ (for FIG. 5B) and a respective combined PPG sub-signal $Px_{c1}$, $Px_{c2}$ (in this embodiment the trimmed mean of the respective normalized PPG sub-signals). The normalized PPG sub-signals shown in FIG. 5A are derived from a remote PPG signal obtained from a subjects' hand, and the normalized PPG sub-signals shown in FIG. 5B are derived from a remote PPG signal obtained from a subjects' face. Although the individual normalized PPG sub-signals differ greatly, the enhanced waveforms, i.e. the combined PPG sub-signals reproduced nicely from a second measurement. Also the waveforms, obtained from the hand and the face, are different suggesting that these waveforms are physiologically meaningful.

A number of obtained combined PPG sub-signals $P1_c$, $P2_c, \ldots, Pm_c$ are then consecutively arranged to obtain an enhanced PPG signal from which a desired vital sign 31, such as the heart rate, breathing rate, (arterial) blood oxygen saturation, is finally derived by a vital sign processor 30. Preferably, a known method, as explained above, is used for this purpose.

Generally, the vital signs are obtained from the original PPG signal, one or more combined PPG sub-signals or an enhanced PPG signal obtained by consecutively arranging a number of combined PPG sub-signals. In another implementation than the above explained implementation, a combined PPG sub-signal (e.g. a single period) is computed and displayed (preferably normalized in time and amplitude) in addition to the original PPG signal so that the shape information could be observed from the combined PPG sub-signal, while the regularity could be observed from the original PPG signal.

The various units of the device 12a may be comprised in one or multiple digital or analog processors depending on how and where the invention is applied. The different units may completely or partly be implemented in software and carried out on a personal computer connected to a device for obtaining image frames of a subject, such as a camera device. Some or all of the required functionality may also be implemented in hardware, e.g. in an application specific integrated circuit (ASIC) or in a field programmable gate array (FPGA).

Figure 6:
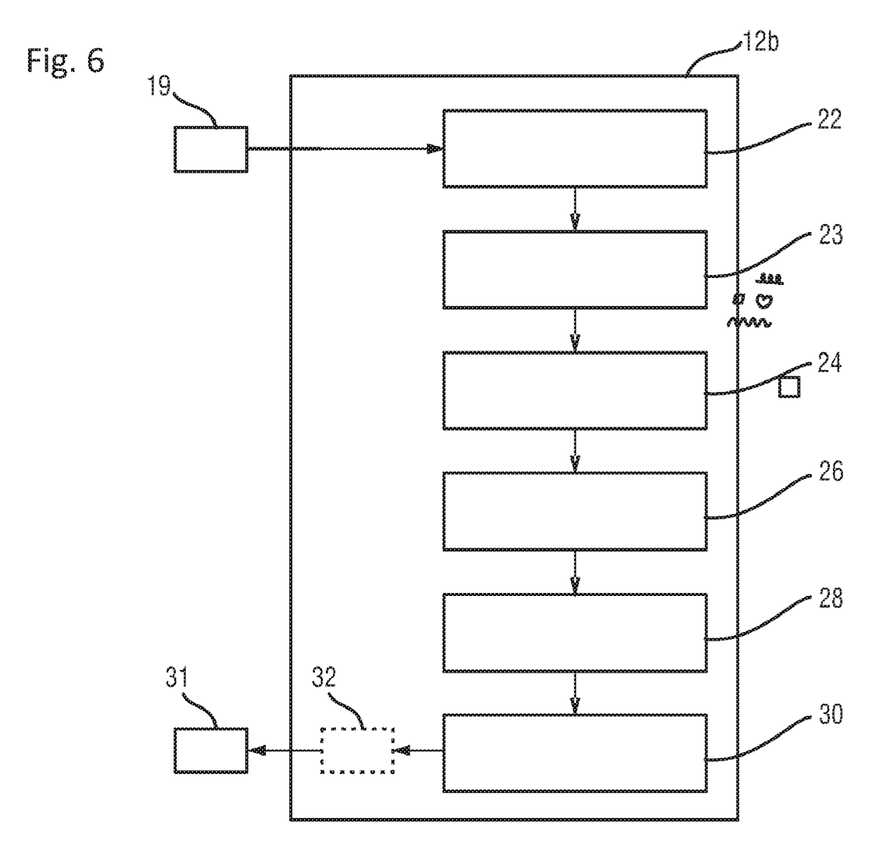
FIG. 6 shows a schematic diagram of a second embodiment of a device according to the present invention.

Another embodiment 12b of the device according to the present invention is depicted in FIG. 6. According to this embodiment a filter 23 for low-pass (or band-pass) filtering the received PPG signal 19 is provided, and the filtered PPG signal is used for subsequent processing. Further, in the filter 23 a running average of the raw, low-pass-filtered PPG signal is subtracted (as a kind of de-trending) from the PPG signal (which subtraction may not be necessary if a band-pass filter is used for filtering the PPG signal). This eliminates low-frequent variations and the DC signal content of the PPG signal from the filtered PPG signal. As explained above, extrema or zero-crossings of the filtered and de-trended PPG signal are then determined, e.g. with a positive and/or negative first derivative (typically the zero-crossing on the steepest part of the PPG signal). Subsequently, a number of recently obtained PPG sub-signals between two of such zero-crossings are averaged, e.g. as explained above, to obtain an improved (combined) PPG sub-signal and, finally, an enhanced PPG signal. Prior to the averaging, the PPG sub-signals pieces are first normalized to have substantially the same amplitude and/or time duration. The enhanced PPG signal may be shown instead or along with the raw (initially received) PPG signal to add waveform information.

Figure 7:
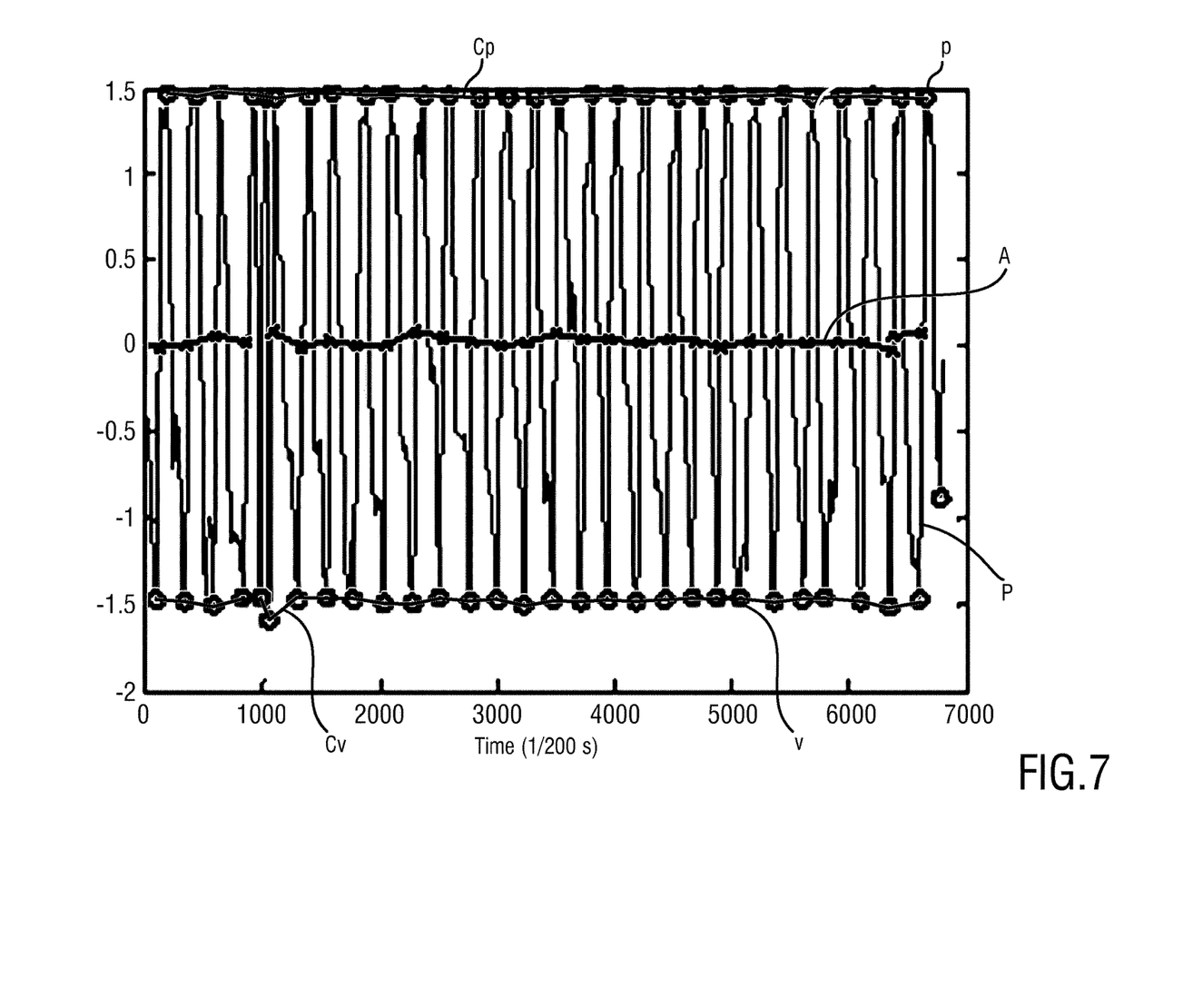
FIG. 7 shows a diagram illustrating another embodiment of processing a PPG signal according to the present invention.

In still another embodiment, which generally has the same or similar elements as the embodiment shown in FIG. 6, the raw, though optionally band-pass filtered, PPG signal is used as input to the signal partitioning unit 24, including a peak and valley detector (or being configured to detect peaks and valleys) in this embodiment. This peak and valley detector may be a more advanced extrema detector and use inhibition intervals to inhibit detection of a peak and or valley at too close a distance to an earlier peak or valley. In a successive step, in the normalizing unit 26 a first curve is fitted through the peaks and a second curve is fitted through the valleys. This is illustrated in FIG. 7 depicting the original PPG signal P, the peaks p through which a first curve Cp is fitted, the valleys v through which a second curve Cv is fitted and the average curve A of the first and second curves Cp, Cv.

For every sample of the PPG signal P the average of these two curves Cp, Cv is subtracted, while the resulting value is divided by the momentary difference of the two curves in order to de-trend and amplitude-normalize the PPG signal. This procedure may be repeated a couple of times (fixed number, or until no significant change occurs). This process is somewhat similar to a basic step in Empirical Mode Decomposition (or Hilbert-Huang Transform), where it is used to generate a number of different signal components instead of normalizing a signal. Next, as in the first embodiment, the zero-crossings are used for time-normalization of the signal and a number of recent signal pieces between two such zero-crossings are averaged to obtain an improved waveform.

Figure 8:
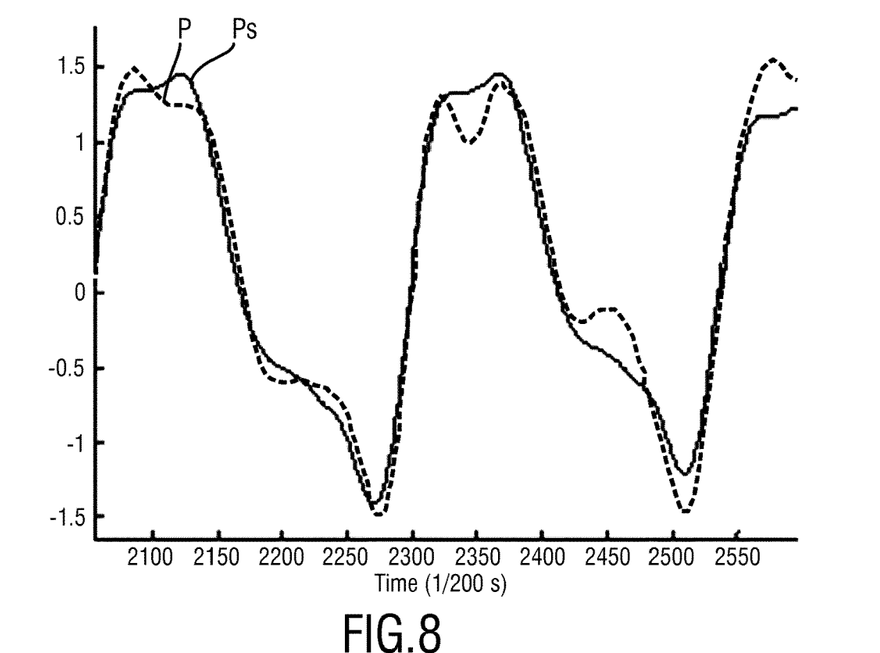
FIG. 8 shows an example of an enhanced PPG signal.

According to still another embodiment, the obtained combined PPG sub-signals, synthesized from a recent history of the PPG signal, can further be used to replace the current PPG signal (completely or only (e.g. distorted) portions of it) after adapting its duration to that of the current interval. The result is shown in FIG. 8, depicting an original PPG signal P and an enhanced PPG signal Ps. To this end, it is possible to start the combination process after a sufficient number of periods (option 1) or to start combining as soon as the history is at least two periods (option 2). Furthermore, the combination may optionally involve a fixed number of periods for option 1, a growing number of periods for option 2, or a weighting may be used where the contribution to the trimmed mean reduces for periods more distant in time. The idea of the combination is thus to simply replace the most recent period(s) of the PPG signal (that would normally be shown on a monitor) by the enhanced period(s) after scaling it (them) back to match the duration (and possibly even the amplitude) of the current PPG period(s).

It has been found that the resulting pulse signal waveform from the above embodiment reproduces when measured at the same body part (e.g. a hand at different days from the same person), while being different for different body parts (e.g. a face and a hand). This strongly suggests the synthetic waveform (i.e. the enhanced PPG signal) to be physiologically meaningful.

Figure 9:
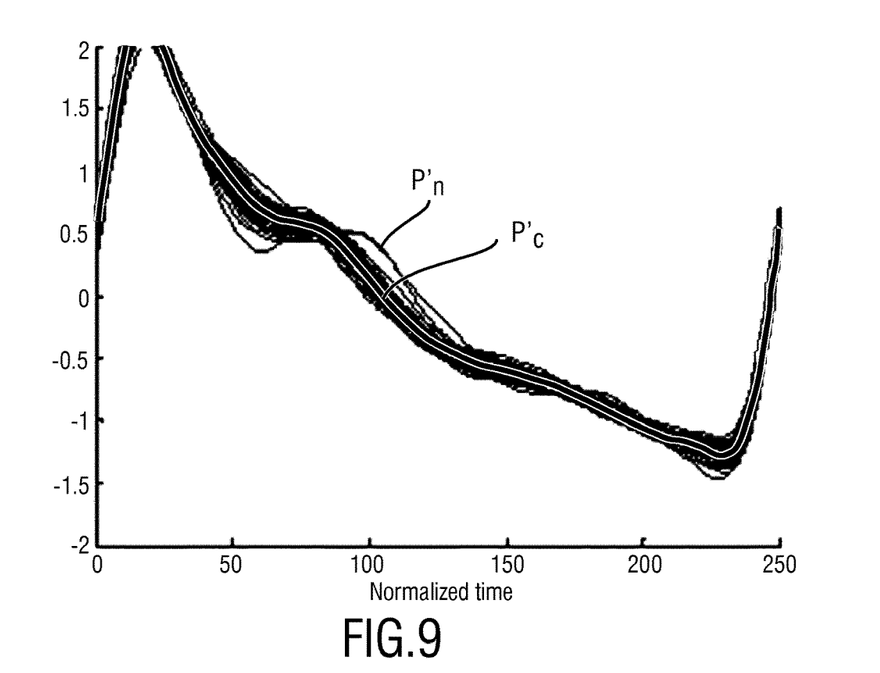
FIG. 9 shows another example of a combined PPG sub-signal.

The present invention may be used with remote PPG signals, but can be equally be applied to enhance signals from a contact PPG sensor as shown in FIG. 9 showing a combined PPG sub-signal $P'_c$ and normalize PPG sub-signals $P'_n$ obtained from a PPG signal or a contact PPG sensor. From this figure it can further be seen that the PPG signal P' from the contact sensor has less noise and shows a distinctly different waveform, likely due to the greater penetration depth of the used infrared light source into the skin. This waveform has already been shown to carry relevant information concerning age, location on the body of the measurement and possible pathologies. Also partial obstruction of some blood vessels may be found by comparing the waveform taken from symmetrical pairs of body parts, e.g. comparing two hands or two feet.

The resulting waveforms for remote PPG contain lower amplitude harmonics than what is typically seen from a contact sensor and the shape therefore is different. This may possibly be caused by the shallow measurement depth (green light has a limited penetration depth into the skin) due to which only the smallest blood vessels are reached where the high frequencies (harmonics of the pulse signal) are dampened. To allow for easier visual discrimination of different waveforms (assuming they have diagnostic value) a HF boosting filter 32 (as optionally indicated in FIG. 6) may be provided for boosting the enhanced PPG signal.

Further, the enhanced PPG signal may also be used to more reliably find the amplitude of the PPG signal in the individual color channels. This could be relevant for SpO2 measurement where finding the correct amplitude of the pulse in the red spectral range (SpO2 is measured as the ratio of relative amplitude in red and infrared) is often complicated by the low amplitude and consequently a poor SNR. Using the correlation of the red PPG signal and the infrared PPG signal with the enhanced PPG signal, from the same, a nearby wavelength, or even a combination of wavelengths, could reduce the influence of noise. In this case the SpO2 is derived from the ratio of the correlations of normalized red and infrared PPG signals with the enhanced PPG signal.

In yet another embodiment, an enhanced PPG signal generated from a green PPG signal (high amplitude) or from an infrared (IR) PPG signal (uniform spatial distribution), or even an enhanced PPG signal derived from a combination of two, or more wavelengths can be used during matched filtering of a red PPG signal. In this case, the "original" PPG signals in the red and IR spectral ranges are used, cleaned using a matched filter with an enhanced PPG signal in the green or/and IR spectral range. In an embodiment a certain recent length of the enhanced PPG signal is taken, possibly windowed with a Hanning-window, and the raw PPG signals from the different color-channels are convolved with this filter kernel.

Although the described processing can be applied to all time-varying vital signs, meaningful results are most likely for near periodical vital signs, such as pulse waves or Traube Hering Mayer waves, and possibly also for signals like respiration that vary a bit more in shape from cycle-to-cycle.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

As used herein, the term "computer" stands for a large variety of processing devices. In other words, also mobile devices having a considerable computing capacity can be referred to as computing device, even though they provide less processing power resources than standard desktop computers. Furthermore, the term "computer" may also refer to a distributed computing device which may involve or make use of computing capacity provided in a cloud environment.

Any reference signs in the claims should not be construed as limiting the scope.

The invention claimed is:

1. A device for determining vital signs of a subject comprising:
   a controller with a memory that stores instructions;
   a processor that executes the instructions, wherein, when executed by processor, the instructions cause the controller to execute a process comprising:
   receiving a periodic photoplethysmographic (PPG) signal obtained from a subject by a PPG measurement;
   partitioning the PPG signal in time into a plurality of PPG sub-signals respectively covering a half period of the PPG signal;
   normalizing in time and/or amplitude the PPG signal in advance of the partitioning and/or the PPG sub-signals to obtain normalized PPG sub-signals;
   combining the normalized PPG sub-signals to obtain one or more combined PPG sub-signals; and
   deriving a desired vital sign of the subject from the one or more combined PPG sub-signals or an enhanced PPG signal obtained by consecutively arranging a plurality of the combined PPG sub-signals.

2. The device as claimed in claim 1, wherein said combining further comprises consecutively arranging the combined PPG sub-signals according to a chronological order of the normalized PPG sub-signals, from which they have been obtained.

3. The device as claimed in claim 1, wherein said combining further comprises combining a predetermined number of consecutive normalized PPG sub-signals arranged within a time window to obtain a combined PPG sub-signal, wherein the time window is shifted in time for each combined PPG sub-signal.

4. The device as claimed in claim 1, wherein the partitioning further comprises detecting zero-crossings and/or extrema of the PPG signal, and using the detected zero-crossings and/or extrema for partitioning the PPG signal.

5. The device as claimed in claim 1, wherein said normalizing the PPG signal in advance of the partitioning further comprises: detecting extrema of the PPG signal, fitting a first curve through detected peaks and a second curve through detected valleys; subtracting a momentary average value of the first and second curves from a momentary signal value of the PPG signal; and dividing a momentary resulting value by a momentary difference value of the first and second curves to obtain a normalized signal value of the PPG signal.

6. The device as claimed in claim 1, wherein said normalizing further comprises repeating the normalizing until a stop condition is met or normalized signal value obtained from the normalizations converge.

7. The device as claimed in claim 1, wherein said combining further comprises generating an average, a weighted average or a trimmed mean of two or more normalized PPG sub-signals.

8. The device as claimed in claim 1, wherein said combining further comprises generating a weighted average or a trimmed mean of two or more normalized PPG sub-signals, wherein the weight for weighting normalized PPG sub-signals decreases with a time-distance to a current time interval.

9. The device as claimed in claim 1, further comprising a filter for low-pass or band-pass filtering the received PPG signal, wherein the filtered PPG signal is used for subsequent processing.

10. The device as claimed in claim 1, wherein said combining further comprises scaling the period of the combined PPG sub-signals in time to match the period of a current time interval and to consecutively arrange a number of the scaled combined PPG sub-signals to obtain the enhanced PPG signal.

11. The device as claimed in claim 1, further comprising a high frequency (HF) boosting filter for boosting of high-frequency harmonics in the PPG sub-signals and/or the enhanced PPG signal, wherein said filtered PPG signal is used for subsequent processing.

12. The device as claimed in claim 1, further comprising an imaging unit for acquiring image frames of a subject, and the process further comprises:
deriving a PPG signal from a skin portion of the subject shown in the image frames and for providing the PPG signals to an interface.

13. The device as claimed in claim 1, further comprising a PPG sensor for acquiring PPG signals from a PPG measurement at a skin portion of the subject and for providing the PPG signals to a interface.

14. A method for determining vital signs of a subject, the method comprising:
receiving a periodic photoplethysmographic (PPG) signal obtained from the subject by a PPG measurement;
partitioning the PPG signal in time into a plurality of PPG sub-signals respectively covering a half period of the PPG signal;
normalizing in time and/or amplitude the PPG signal in advance of the partitioning and/or the PPG sub-signals to obtain normalized PPG sub-signals;
combining the normalized PPG sub-signals to obtain one or more combined PPG sub-signal; and
deriving a desired vital sign from the one or more combined PPG sub-signals or an enhanced PPG signal obtained by consecutively arranging a plurality of the combined PPG sub-signals.

15. A non-transitory computer-readable medium storing a computer program executable on a computer processor, which when executed by the computer processor cause a computer to carry out the steps of the method as claimed in claim 14.

* * * * *